US011180516B2

United States Patent
Nakatsui et al.

(10) Patent No.: US 11,180,516 B2
(45) Date of Patent: Nov. 23, 2021

(54) PHOSPHINE TRANSITION METAL COMPLEX, METHOD FOR PRODUCING SAME, AND ANTICANCER AGENT

(71) Applicant: Nippon Chemical Industrial Co., Ltd., Tokyo (JP)

(72) Inventors: Kazuhiro Nakatsui, Tokyo (JP); Chiaki Ono, Tokyo (JP); Nobuhiko Oohara, Tokyo (JP); Tsuneo Imamoto, Tokyo (JP); Hiroaki Konishi, Tokyo (JP); Hikaru Abutani, Tokyo (JP)

(73) Assignee: NIPPON CHEMICAL INDUSTRIAL CO., LTD., Tokyo (JP)

( * ) Notice: Subject to any disclaimer, the term of this patent is extended or adjusted under 35 U.S.C. 154(b) by 0 days.

(21) Appl. No.: 17/269,318

(22) PCT Filed: Sep. 26, 2019

(86) PCT No.: PCT/JP2019/037900
§ 371 (c)(1),
(2) Date: Feb. 18, 2021

(87) PCT Pub. No.: WO2020/071241
PCT Pub. Date: Apr. 9, 2020

(65) Prior Publication Data
US 2021/0253612 A1    Aug. 19, 2021

(30) Foreign Application Priority Data

Oct. 3, 2018    (JP) .............................. JP2018-188266

(51) Int. Cl.
| C07F 9/50 | (2006.01) |
| C07F 9/6509 | (2006.01) |
| A61P 35/00 | (2006.01) |

(52) U.S. Cl.
CPC ............ *C07F 9/5045* (2013.01); *A61P 35/00* (2018.01); *C07F 9/505* (2013.01); *C07F 9/650994* (2013.01)

(58) Field of Classification Search
CPC .. C07F 9/5045; C07F 9/505; C07F 9/650994; A61P 35/00
USPC ....................................................... 544/225
See application file for complete search history.

(56) References Cited

U.S. PATENT DOCUMENTS

| 5,843,993 A | 12/1998 | Katti et al. |
| 6,159,957 A | 12/2000 | Berners-Price et al. |
| 2010/0048894 A1 | 2/2010 | Kodama et al. |

FOREIGN PATENT DOCUMENTS

| JP | 61-10594 A | 1/1986 |
| JP | 2007-320909 A | 12/2007 |
| WO | 96/17856 A1 | 6/1996 |

OTHER PUBLICATIONS

International Search Report dated Nov. 26, 2019, issued in counterpart application No. PCT/JP2019/037900 (2 pages).
Decision to Grant a Patent dated Nov. 24, 2020, issued in counterpart Japanese Patent Application No. 2018-188266, w/English translation (5 pages).

(Continued)

*Primary Examiner* — Kristin A Vajda
(74) *Attorney, Agent, or Firm* — Westerman, Hattori, Daniels & Adrian, LLP

(57) ABSTRACT

The phosphine transition metal complex of the present invention is represented by formula (1).

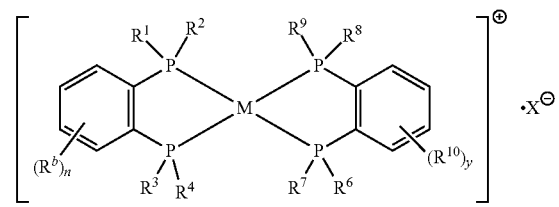

Preferably, $R^1$ and $R^6$ are identical groups, $R^2$ and $R^7$ are identical groups, $R^3$ and $R^8$ are identical groups, $R^4$ and $R^9$ are identical groups, $R^5$ and $R^{10}$ are identical groups, and n and y are identical numbers. The phosphine transition metal complex is suitably obtained by reacting a phosphine derivative represented by formula (2) and a phosphine derivative represented by formula (3) with a salt of a transition metal of gold, copper or silver.

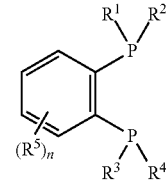

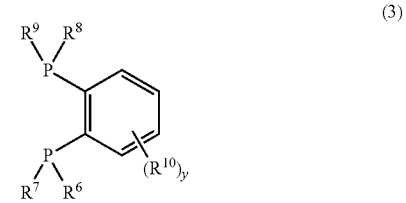

See the description for the meanings of the symbols in each formula.

10 Claims, No Drawings

(56) References Cited

OTHER PUBLICATIONS

Baker et al., "Coinage metal-catalyzed hydroboration of imines", Journal of Organometallic Chemistry, 1995, vol. 498, No. 2, pp. 109-117, cited in ISR and JP Decision to Grant a Patent (9 pages).
Salem et al., "Rearrangements of Tetrahedral Copper(I) and Silver(I) Complexes Containing Chelating Bis(tertiary arsines and phosphines)", Inorganic Chemistry, 1988, vol. 27, No. 17, pp. 3029-3032, cited in JP Decision to Grant a Patent (4 pages).

PHOSPHINE TRANSITION METAL COMPLEX, METHOD FOR PRODUCING SAME, AND ANTICANCER AGENT

TECHNICAL FIELD

The present invention relates to a novel phosphine transition metal complex, a method for producing the same, and an anticancer agent.

BACKGROUND ART

Conventionally, cisplatin is well known as a substance having high anticancer activity against cancer cells and is now a major anticancer agent.

It is also known that various phosphine transition metal complexes, including 1,2-bis(diphenylphosphino)ethane, are compounds having anticancer activity comparable to cisplatin (see, e.g., Patent Literatures 1 and 2).

In addition, the present applicant has previously proposed an anticancer agent containing a phosphine transition metal complex represented by the following formula (a) (see Patent Literature 3). In the formula, $R_1$, $R_2$, $R_3$, $R_4$ are alkyl groups or the like. M is gold, copper or silver, and $X^-$ is an anion. This anticancer agent has high anticancer activity compared to Taxol (registered trademark) and platinum formulations such as cisplatin which are conventionally used anticancer agents.

[Formula 1]

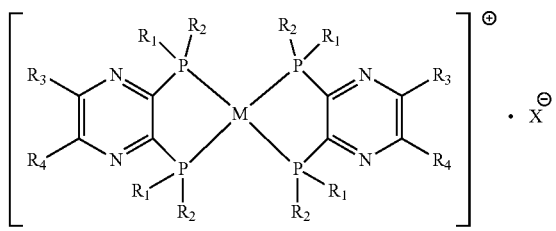

(a)

CITATION LIST

Patent Literatures

Patent Literature 1: WO 96/17856 A1
Patent Literature 2: Japanese Patent Laid-Open No. 61-10594
Patent Literature 3: US 2010/048894 A1

SUMMARY OF INVENTION

The phosphine transition metal complex of Patent Literature 3 has low solubility in water. For this reason, when a solution of the drug is administered to a living body, there are possibilities that the deposition of phosphine transition metal complexes may occur in the body and the anticancer effect may be impaired. Thus, there is a problem that the form of administration to the living body is quite limited.

Considering the current state above, an object of the present invention is to provide a novel phosphine transition metal complex having excellent solubility in an aqueous solvent, an industrially advantageous production method thereof, and an anticancer agent having excellent anticancer activity.

The present invention provides a phosphine transition metal complex represented by formula (1):

[Formula 2]

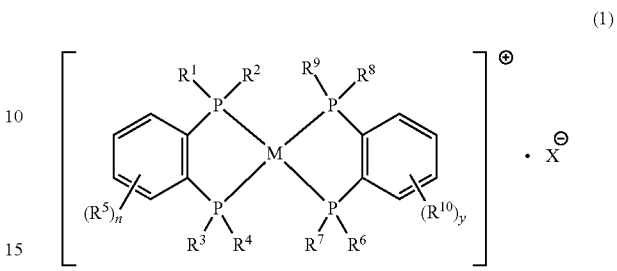

(1)

wherein, $R^1$, $R^2$, $R^3$, $R^4$, $R^6$, $R^7$, $R^8$ and $R^9$ each independently represent an optionally substituted linear or branched alkyl group having 1 to 10 carbon atoms, an optionally substituted cycloalkyl group, or an optionally substituted adamantyl group; $R^5$ and $R^{10}$ each independently represent a monovalent substituent; n and y each independently represent an integer of 0 to 4; M represents a transition metal atom selected from the group of gold, copper and silver; and $X^-$ represents an anion.

The present invention also provides a method for producing a phosphine transition metal complex, comprising reacting
a phosphine derivative represented by formula (2):

[Formula 3]

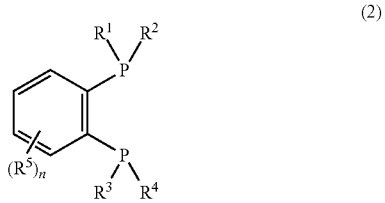

(2)

wherein, $R^1$, $R^2$, $R^3$ and $R^4$ each independently represent an optionally substituted linear or branched alkyl group having 1 to 10 carbon atoms, an optionally substituted cycloalkyl group, or an optionally substituted adamantyl group; $R^5$ represents a monovalent substituent; and n represents an integer of 0 to 4,
a phosphine derivative represented by formula (3):

[Formula 4]

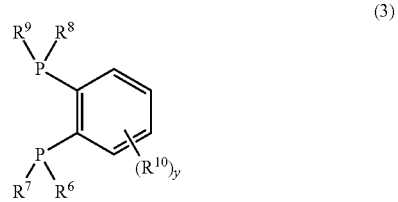

(3)

wherein $R^6$, $R^7$, $R^8$ and $R^9$ each independently represent an optionally substituted linear or branched alkyl group having 1 to 10 carbon atoms, an optionally substituted cycloalkyl group, or an optionally substituted adamantyl group; $R^{10}$ represents a monovalent substituent; and y represents an integer of 0 to 4, and a salt of a transition metal of gold, copper, or silver to obtain a phosphine transition metal complex represented by formula (1):

[Formula 5]

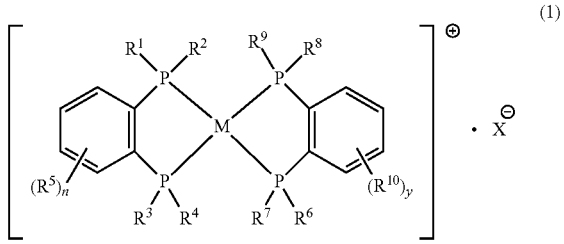

wherein $R^1$, $R^2$, $R^3$, $R^4$, $R^6$, $R^7$, $R^8$ and $R^9$ each independently represent an optionally substituted linear or branched alkyl group having 1 to 10 carbon atoms, an optionally substituted cycloalkyl group, or an optionally substituted adamantyl group; $R^5$ and $R^{10}$ each independently represent a monovalent substituent; n and y each independently represent an integer of 0 to 4; M represents a transition metal atom selected from the group of gold, copper, and silver; and $X^-$ represents an anion.

The present invention further provides a medicament, particularly an anticancer agent, containing the phosphine transition metal complex. The present invention also provides use of the phosphine transition metal complex for production of a medicament, particularly an anticancer agent.

DESCRIPTION OF EMBODIMENTS

Hereinafter, the present invention will be described based on the preferred embodiments thereof.

The phosphine transition metal complex of the present invention is a phosphine transition metal complex represented by the following formula (1).

[Formula 6]

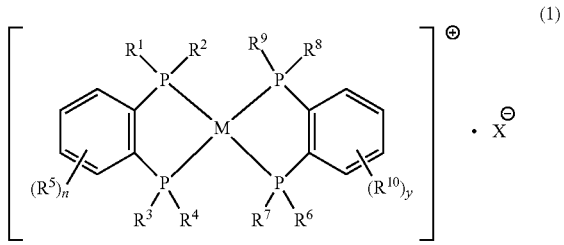

In formula (1), $R^1$ to $R^4$, $R^6$ to $R^9$ each represent an optionally substituted linear or branched alkyl group having 1 to 10 carbon atoms, an optionally substituted cycloalkyl group, or an optionally substituted adamantyl group. $R^1$ to $R^4$, $R^6$ to $R^9$ each may be identical groups to each other or different groups from each other.

Examples of the alkyl group having 1 to 10 carbon atoms represented by $R^1$ to $R^4$, $R^6$ to $R^9$ include a methyl group, an ethyl group, an isopropyl group, an n-propyl group, an isobutyl group, an n-butyl group, a sec-butyl group, a tert-butyl group, a neopentyl group, an isopentyl group, an n-pentyl group, a sec-pentyl group, a tert-pentyl group, a 3-pentyl group, an isohexyl group, an n-hexyl group, a 2-hexyl group, a 3-hexyl group, an isoheptyl group, an n-heptyl group, a 2-heptyl group, a 3-heptyl group, a tert-heptyl group, an n-octyl group, an isooctyl group, a tert-octyl group, a 2-ethylhexyl group, a nonyl group, an isononyl group and a decyl group. The cycloalkyl group represented by $R^1$ to $R^4$, $R^6$ to $R^9$ is preferably a cycloalkyl group having 3 to 10 carbon atoms, more preferably, particularly 5 to 6 carbon atoms. Examples of such cycloalkyl groups include a cyclopentyl group and a cyclohexyl group. When any of $R^1$ to $R^4$, $R^6$ to $R^9$ is a cycloalkyl group having a substituent or an adamantyl group having a substituent, examples of the substituent includes an alkyl group, a nitro group, an amino group, a hydroxyl group, an alkoxy group, a fluoro group, a chloro group, a bromo group, and an iodo group. Examples of the alkyl group as a substituent include those same as the above-described alkyl group having 1 to 10 carbon atoms represented by $R^1$ to $R^4$, $R^6$ to $R^9$. Examples of the alkoxy group as a substituent include those in which an oxygen atom is attached to a carbon atom at the end of the bonding side of the alkyl group having 1 to 10 carbon atoms represented by $R^1$ to $R^4$, $R^6$ to $R^9$. When any of the alkyl group having 1 to 10 carbon atoms represented by $R^1$ to $R^4$, $R^6$ to $R^9$ is an alkyl group having a substituent, examples of the substituent include a trifluoromethyl group. When $R^1$ to $R^4$, $R^6$ to $R^9$ have a substituent and the substituent is a group having a number of carbon atoms, the number of carbon atoms in $R^1$ to $R^4$, $R^6$ to $R^9$, including the number of carbon atoms of the substituent, is preferably 10 or less.

$R^1$ to $R^4$, $R^6$ to $R^9$ described above may be different groups from each other or identical groups to each other. For example, the combinations of $R^1$ to $R^4$ include the following combinations:

(i) $R^1$ to $R^4$ are all identical groups;
(ii) $R^1$ and $R^2$ are identical groups to each other, and $R^3$ and $R^4$ are different groups from each other;
(iii) $R^1$ and $R^2$ are different groups from each other, and $R^3$ and $R^4$ are also different groups from each other;
(iv) $R^1$ and $R^2$ are identical groups, and $R^3$ and $R^4$ are also identical groups, provided that $R^1$ and $R^2$ are not groups identical to $R^3$ and $R^4$;
and the like.

In the present invention, particularly preferably, (iii) $R^1$ and $R^2$ are different groups from each other, and $R^3$ and $R^4$ are also different groups from each other, from the viewpoint of reduced crystallinity due to the collapse of symmetry, resulting in excellent solubility in solvents such as water.

Particularly, when (iii) $R^1$ and $R^2$ are different groups from each other and $R^3$ and $R^4$ are also different groups from each other, preferably, one of $R^1$ and $R^2$ is a short chain alkyl group having 2 or less carbon atoms and the other is a group having 3 or more carbon atoms, and one of $R^3$ and $R^4$ is a short chain alkyl group having 2 or less carbon atoms and the other is a group having 3 or more carbon atoms. Especially preferably, one of $R^1$ and $R^2$ is a methyl group and the other is an optionally substituted branched alkyl group having 3 or more and 10 or less carbon atoms, an optionally substituted cycloalkyl group, or an optionally substituted adamantyl group, and one of $R^3$ and $R^4$ is a methyl group and the other is an optionally substituted branched alkyl group having 3 or more and 10 or less carbon atoms, an optionally substituted cycloalkyl group, or an optionally substituted adamantyl group. Among others, particularly preferably, one of $R^1$ and $R^2$ is a methyl group and the other is an optionally substituted isopropyl group, an optionally substituted t-butyl group, an optionally substituted cyclohexyl group, or an optionally substituted adamantyl group, and one of $R^3$ and $R^4$ is a methyl group and the other is an optionally substituted isopropyl group, an optionally substituted t-butyl group, an optionally substituted cyclohexyl group, or an optionally substituted adamantyl group.

When (iii) $R^1$ and $R^2$ are different groups from each other and $R^3$ and $R^4$ are also different groups from each other, particularly preferably (iii+) $R^1$ and $R^2$, and $R^3$ and $R^4$ are combinations of identical two groups, in that a compound of interest is easily produced, the number of isomers is reduced upon complexing, the identification of the composition is facilitated, and the like.

Similarly, the combinations of $R^8$ to $R^9$ include the following combinations:
(I) $R^6$ to $R^9$ are all identical groups;
(II) $R^6$ and $R^7$ are identical groups, and $R^8$ and $R^9$ are different groups from each other;
(III) $R^6$ and $R^7$ are different groups from each other, and $R^8$ and $R^9$ are also different groups from each other;
(IV) $R^6$ and $R^7$ are identical groups, and $R^8$ and $R^9$ are also identical groups, provided that $R^6$ and $R^7$ are not groups identical to $R^8$ and $R^9$;
and the like In the present invention, particularly preferably, (III) $R^6$ and $R^7$ are different groups from each other, and $R^8$ and $R^9$ are also different groups from each other, from the viewpoint of reduced crystallinity due to the collapse of symmetry, resulting in excellent solubility in solvents such as water.

Particularly, when (III) $R^6$ and $R^7$ are different groups from each other and $R^8$ and $R^9$ are also different groups from each other, preferably, one of $R^6$ and $R^7$ is a short chain alkyl group having 2 or less carbon atoms and the other is a group having 3 or more carbon atoms, and one of $R^8$ and $R^9$ is a short chain alkyl group having 2 or less carbon atoms and the other is a group having 3 or more carbon atoms. Especially preferably, one of $R^6$ and $R^7$ is a methyl group and the other is an optionally substituted branched alkyl group having 3 or more and 10 or less carbon atoms, an optionally substituted cycloalkyl group, or an optionally substituted adamantyl group, and one of $R^8$ and $R^9$ is a methyl group and the other is an optionally substituted branched alkyl group having 3 or more and 10 or less carbon atoms, an optionally substituted cycloalkyl group, or an optionally substituted adamantyl group. Among others, particularly preferably, one of $R^6$ and $R^7$ is a methyl group and the other is an optionally substituted isopropyl group, an optionally substituted t-butyl group, an optionally substituted cyclohexyl group, or an optionally substituted adamantyl group, and one of $R^8$ and $R^9$ is a methyl group and the other is an optionally substituted isopropyl group, an optionally substituted t-butyl group, an optionally substituted cyclohexyl group, or an optionally substituted adamantyl group.

When (III) $R^6$ and $R^7$ are different groups from each other and $R^8$ and $R^9$ are also different groups from each other, preferably, (III+) $R^6$ and $R^7$, and $R^8$ and $R^9$ are combinations of identical two groups, in that a compound of interest is easily produced, the number of isomers is reduced upon complexing, the identification of the composition is facilitated, and the like.

Furthermore, among the compounds of formula (1), those in which $R^1$ and $R^6$ are identical groups, $R^2$ and $R^7$ are identical groups, $R^3$ and $R^8$ are identical groups, $R^4$ and $R^9$ are identical groups, and $R^5$ and $R^{10}$ are identical groups are preferable in that a compound of interest is easily produced.

In the present invention, preferred combinations of $R^1$ to $R^4$, $R^6$ to $R^9$ in formula (1) include the following:
(α) $R^1$ and $R^2$, $R^3$ and $R^4$, $R^6$ and $R^7$, and $R^8$ and $R^9$ are all combinations of an isopropyl group and a methyl group;
(β) $R^1$ and $R^2$, $R^3$ and $R^4$, $R^6$ and $R^7$, and $R^8$ and $R^9$ are all combinations of a t-butyl group and a methyl group;
(γ) $R^1$ and $R^2$, and $R^6$ and $R^7$ are both combinations of a cyclohexyl group and a methyl group; and $R^3$ and $R^4$, and $R^8$ and $R^9$ are both combinations of an adamantyl group and a methyl group;
(δ) $R^1$ to $R^4$, $R^6$ to $R^9$ are all isopropyl groups; and
(ε) $R^1$, $R^2$, $R^6$ and $R^7$ are methyl groups, and $R^3$, $R^4$, $R^8$ and $R^9$ are combinations of t-butyl groups.

In the present invention, for the combinations of $R^1$ to $R^4$, $R^6$ to $R^9$ in formula (1), particularly preferably, (β) $R^1$ and $R^2$, $R^3$ and $R^4$, $R^6$ and $R^7$, and $R^8$ and $R^9$ are all combinations of a t-butyl group and a methyl group, from the viewpoints of the established stereoselective synthesis method of the corresponding phosphine site, obtaining a high purity complex without mixing of isomers, high solubility in an aqueous system, and easy production of a compound of interest.

$R^5$ and $R^{10}$ in formula (1) each independently represent a monovalent substituent. Examples of the monovalent substituent represented by $R^5$ and $R^{10}$ include a linear or branched alkyl group having 1 to 6 carbon atoms, a cycloalkyl group, a nitro group, an amino group, a hydroxyl group, an alkoxy group, a fluoro group, a chloro group, a bromo group, an iodo group, and a silyl group. The number of carbon atoms in the cycloalkyl group is preferably 3 or more and 8 or less. The number of carbon atoms in the alkoxy group is preferably 1 or more and 8 or less. The monovalent substituent represented by $R^5$ and $R^{10}$ is preferably an organic group, and more preferably, particularly an organic group having 1 or more and 10 or less carbon atoms. $R^5$ and $R^{10}$ are preferably identical groups in that the phosphine transition metal complex is easily produced.

n and y in formula (1) each independently represent an integer of 0 to 4, preferably an integer of 0 to 2. n and y are preferably identical numbers in that the phosphine transition metal complex is easily produced. For example, n and y may both be 0.

M in formula (1) represents a transition metal atom selected from the group of gold, copper, and silver, and is preferably a gold atom from the viewpoint of use as an anticancer agent.

In formula (1), $X^-$ represents an anion, and examples thereof include a chlorine ion, a bromine ion, an iodine ion, a boron tetrafluoride ion, a hexafluorophosphate ion, and a perchlorate ion. Of these, $X^-$ is preferably a chlorine ion, bromine ion or iodine ion, from the viewpoint of increased solubility in an aqueous system.

In the present invention, in terms of synthesis, a particularly preferred phosphine transition metal complex represented by formula (1) is a compound having an asymmetric center on four phosphorus atoms in the formula. As such compounds, a compound having an asymmetric center on a phosphorus atom represented by the following formula (1') is especially preferred.

[Formula 7]

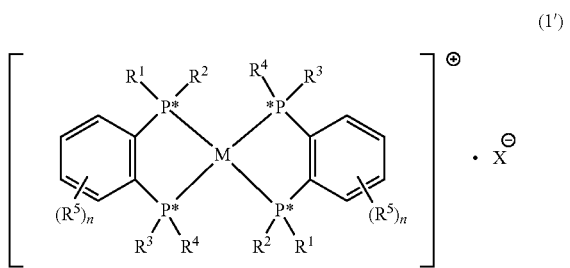

In formula (1'), $R^1$, $R^2$, $R^3$, $R^4$, $R^5$, n, and $X^-$ are the same as defined in formula (1), provided that $R^1$ and $R^2$ are different groups from each other, and $R^3$ and $R^4$ are different groups from each other. Asterisk (*) represents an asymmetric phosphorus atom.

Although there are numerous isomers of the phosphine transition metal complex represented by formula (1) having four asymmetric phosphorus atoms, including the phosphine transition metal complex represented by formula (1'), the types of these isomers are not particularly limited in the present invention. Specifically, these isomers may have configurations on the phosphorus atoms composed of single enantiomers such as (R,R) (R,R) or (S,S) (S,S), composed of mesomers of one another such as (R,S) (S,R), or composed of one enantiomer and a mesomer thereof such as (R,R) (S,R). The isomers may also have a configuration composed of enantiomers which are different in absolute configuration on the phosphorus atoms, such as (R,R) (S,S).

In the phosphine transition metal complex represented by formula (1) having four asymmetric phosphorus atoms, those in which an absolute configuration on the phosphorus atom to which $R^1$ and $R^2$ are bound and an absolute configuration on the phosphorus atom to which $R^6$ and $R^7$ are bound are identical, and an absolute configuration on the phosphorus atom to which $R^3$ and $R^4$ are bound and an absolute configuration on the phosphorus atom to which $R^8$ and $R^9$ are bound are identical, are especially preferred in that a compound of interest is easily produced.

Especially, those in which an absolute configuration on the phosphorus atom to which $R^1$ and $R^2$ are bound, an absolute configuration on the phosphorus atom to which $R^3$ and $R^4$ are bound, an absolute configuration on the phosphorus atom to which $R^6$ and $R^7$ are bound, and an absolute configuration on the phosphorus atoms to which $R^8$ and $R^9$ are bound in formula (1) are all identical absolute configurations, such as (R,R) (R,R) and (S,S) (S,S) as described above, are preferred in that a compound of interest is easily produced, and the purity is improved due to substantially no isomers upon complexing.

The phosphine transition metal complex represented by formula (1) is suitably produced by reacting a phosphine derivative represented by the following formula (2), a phosphine derivative represented by the following formula (3), and a salt of a transition metal of gold, copper or silver.

[Formula 8]

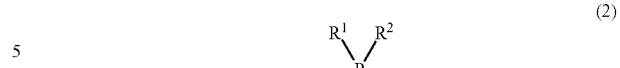

[Formula 9]

In formula (2), $R^1$, $R^2$, $R^3$, $R^4$, $R^5$ and n are the same as defined in $R^1$, $R^2$, $R^3$, $R^4$, $R^5$ and n in formula (1). In other words, $R^1$, $R^2$, $R^3$, $R^4$, $R^5$ and n in formula (2) correspond to $R^1$, $R^2$, $R^3$, $R^4$, $R^5$ and n in formula (1), respectively.

Similarly, in formula (3), $R^6$, $R^7$, $R^8$, $R^9$, $R^{10}$ and y are the same as defined in $R^6$, $R^7$, $R^8$, $R^9$, $R^{10}$ and y in formula (1). In other words, $R^6$, $R^7$, $R^8$, $R^9$, $R^{10}$ and y in formula (3) correspond to $R^6$, $R^7$, $R^8$, $R^9$, $R^{10}$ and y in formula (1), respectively.

When the phosphine derivative represented by formula (2) and the phosphine derivative represented by formula (3) are the same compound, the phosphine transition metal complex represented by formula (1) described above is produced by reacting a phosphine derivative represented by the following formula (2) with a salt of a transition metal of gold, copper or silver. In this case, as the phosphine transition metal complex represented by formula (1), a phosphine transition metal complex in which $R^1$ and $R^6$ are identical groups, $R^2$ and $R^7$ are identical groups, $R^3$ and $R^8$ are identical groups, $R^4$ and $R^9$ are identical groups, $R^5$ and $R^{10}$ are identical groups, and n and y are identical numbers (hereinafter, the phosphine transition metal complex is also referred to as "symmetric form") is obtained.

When the phosphine derivative represented by formula (2) and the phosphine derivative represented by formula (3) are different compounds, the phosphine derivative represented by formula (2) and the phosphine derivative represented by formula (3) may be reacted simultaneously with a salt of a transition metal of gold, copper or silver, but preferably in terms of reaction efficiency, the phosphine derivative represented by formula (2) is first reacted with a salt of a transition metal of gold, copper or silver, and then the resulting reaction product is reacted with the phosphine derivative represented by formula (3).

The phosphine derivative represented by formula (2) and the phosphine derivative represented by formula (3) are known compounds, and can be produced by known production methods (see, for example, Japanese Patent Laid-Open No. 2000-319288, Japanese Patent Laid-Open No. 2012-17288, ORGANIC LETTERS, 2006, Vol. 8, No. 26, 6103-6106, or the like).

In order to obtain, as the phosphine transition metal complex represented by formula (1), an optically active compound of the phosphine transition metal complex having an asymmetric center on four phosphorus atoms, a phosphine derivative represented by formula (2) wherein $R^1$ and $R^2$ are different from each other and $R^3$ and $R^4$ are different from each other and a phosphine derivative represented by formula (3) wherein $R^6$ and $R^7$ are different from each other and $R^8$ and $R^9$ are different from each other may be used in the method for producing a phosphine transition metal complex described above.

In order to obtain, as an optically active compound of the phosphine transition metal complex, for example, a phosphine transition metal complex represented by formula (1'), an optically active compound of a phosphine derivative represented by the following formula (2'), which is an optically active compound of a phosphine derivative represented by formula (2), may be used:

[Formula 10]

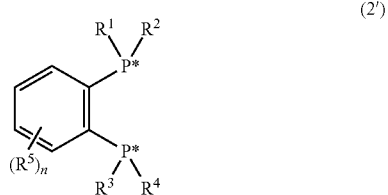

(2')

wherein $R^1$, $R^2$, $R^3$, $R^4$, $R^5$, and n are the same as defined in formula (1'); and asterisk (*) represents an asymmetric phosphorus atom.

An optically active compound of a phosphine derivative represented by formula (2') can be produced, for example, in accordance with reaction scheme (1) below. A phosphine derivative represented by formula (2) other than the optically active compound represented by formula (2') and a phosphine derivative represented by formula (3) can also be produced in the same manner as in reaction scheme (1) below by appropriately varying a phosphine-borane compound (3), a compound of formula (6) or a compound of formula (8), or the like, depending on the compound to be obtained:

Reaction Scheme (1)

[Formula 11]

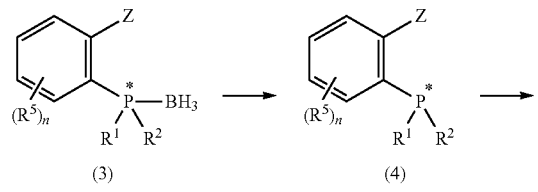

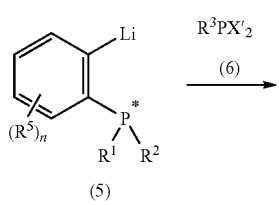

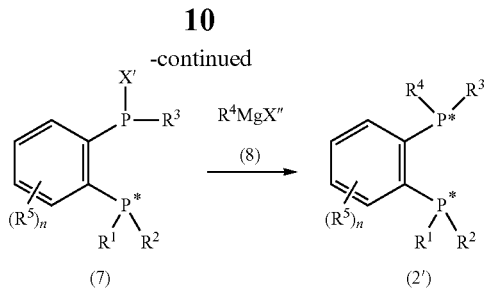

wherein $R^1$, $R^2$, $R^3$, $R^4$, $R^5$, n, and * are the same as defined in formula (1'); and Z, X' and X" each represent a halogen atom.

Examples thereof include a method in which the phosphine-borane compound (3) is de-boranized with 1,4-diazabicyclo[2.2.2]octane (DABCO) or the like, then lithiated with a lithiating agent such as butyl lithium, and then the reaction product (5) is reacted with dihalogenophosphine represented by formula (6): $R^3PX'_2$ (wherein $R^3$ is the same as defined above; and X' represents a halogen atom) to obtain a reaction product (7); then the reaction product (7) is reacted with a Grignard reagent represented by formula (8): $R^4MgX''$ (wherein $R^4$ is the same as defined above; and X" represents a halogen atom) (See Japanese Patent Laid-Open No. 2012-17288). The phosphine-borane compound (3) can be produced by the method described in Japanese Patent Laid-Open No. 2012-17288.

The salt of a transition metal according to the method for producing a phosphine transition metal complex of the present invention is a salt between an anion and a gold ion, a copper ion or a silver ion, and examples thereof include a halide, a nitrate salt, a perchlorate salt, a boron tetrafluoride salt, and a hexafluorophosphate salt of gold, copper or silver. The salt of a transition metal of gold, copper or silver may be two or more transition metal salts that are different in one or both of the transition metal species and the anion.

Preferred examples of the salt of the transition metal of gold include gold(I) chloride acid, gold(I) chloride, or tetrabutylammonium chloride-gold(I) chloride (see "The fifth series of experimental chemistry 21", The Chemical Society of Japan, Maruzen Publishing Co., Ltd., Mar. 30, 2004, pp. 366-380; Aust. J. Chemm., 1997, 50, pp. 775-778). Preferred examples of the salt of the transition metal of copper include copper(I) chloride, copper(I) bromide, and copper(I) iodide ("The fifth series of experimental chemistry 21", The Chemical Society of Japan, Maruzen Publishing Co., Ltd., Mar. 30, 2004, pp. 349-361). Preferred examples of the salt of the transition metal of silver include silver(I) chloride, silver(I) bromide, and silver(I) iodide ("The fifth series of experimental chemistry 21", The Chemical Society of Japan, Maruzen Publishing Co., Ltd., Mar. 30, 2004, pp. 361-366). Note that the salt of a transition metal according to the method for producing a phosphine transition metal complex of the present invention may be an anhydride or a hydrate.

When obtaining the symmetric form described above as a phosphine transition metal complex represented by formula (1), the symmetric form described above is obtained by reacting a phosphine derivative represented by formula (2) with a salt of a transition metal of gold, copper or silver, at the molar ratio of the phosphine derivative represented by formula (2) to the transition metal of a salt of a transition metal of gold, copper or silver is 1 to 5 fold, preferably 1.8 to 2.2 fold molar amounts, in a solvent such as acetone, acetonitrile, methanol, ethanol, or dichloromethane at a reaction temperature of −20 to 60° C., preferably 0 to 25° C., for a reaction time of 0.5 to 48 hours, preferably 1 to 3 hours. The reaction is preferably performed under an inert atmosphere such as a nitrogen atmosphere. After the reaction is completed, purification by conventional methods may be performed as needed. When obtaining a phosphine transition metal complex represented by formula (1) other than the symmetric form, the phosphine transition metal complex can be produced by reacting the transition metal of a salt of a transition metal of gold, copper or silver with a phosphine derivative represented by formula (2) at a molar ratio of about 1:1, e.g., a molar ratio of 1:0.9 to 1.1 fold, and then reacting the resulting reaction product with a phosphine derivative represented by formula (3) at a molar ratio of about 1:1, e.g., a molar ratio of 1:0.9 to 1.1 fold.

Furthermore, the anion of the phosphine transition metal complex represented by formula (1) obtained by the method for producing a phosphine transition metal complex of the present invention can be converted into another anion to produce a phosphine transition metal complex represented by formula (1) having a desired anion.

For example, first, a phosphine transition metal complex wherein $X^-$ in formula (1) is a halogen ion is synthesized by the method for producing a phosphine transition metal complex of the present invention, then the phosphine transition metal complex wherein $X^-$ in formula (1) is a halogen ion is reacted in an appropriate solvent with an inorganic acid, an organic acid or an alkali metal salt thereof having a desired anion, thereby a phosphine transition metal complex wherein $X^-$ in formula (1) is a desired anion can be obtained (see Japanese Patent Laid-Open No. 10-147590, Japanese Patent Laid-Open No. 10-114782, and Japanese Patent Laid-Open No. 61-10594).

The phosphine transition metal complex represented by formula (1) has excellent solubility in an aqueous solvent compared to a conventional phosphine transition metal complex represented by formula (a) described above. The phosphine transition metal complex of the present invention has high anticancer activity as described later, thus can be utilized as an anticancer agent. Examples of the aqueous solvent described above include water, a buffer solution, and a physiological salt solution, and those to which various additives have been added. Examples of the buffer solution and the physiological salt solution include, but are not limited to, those described later as a buffer solution or a physiological salt solution used for liquid formulations. Examples of the additive include, but are not limited to, those described later as additives used for solid or liquid formulations.

In other words, the anticancer agent of the present invention contains one or two or more of the phosphine transition metal complexes represented by formula (1).

When the phosphine transition metal complex represented by formula (1) is a phosphine transition metal complex having an asymmetric center on a phosphorus atom, that is, an optically active compound, there are numerous isomers of the phosphine transition metal complex represented by formula (1). The anticancer agent of the present invention may be one or two or more of the isomers.

The types of cancers to which the anticancer agent of the present invention is applied are not particularly limited, and examples thereof include malignant melanoma, malignant lymphoma, gastrointestinal cancer, lung cancer, esophageal cancer, gastric cancer, colorectal cancer, rectal cancer, colon cancer, ureteral tumor, gallbladder cancer, bile duct cancer, biliary cancer, breast cancer, liver cancer, pancreatic cancer, testicular tumor, maxillary cancer, tongue cancer, lip cancer, oral cancer, pharyngeal cancer, laryngeal cancer, ovarian cancer, uterine cancer, prostate cancer, thyroid cancer, brain tumor, Kaposi's sarcoma, hemangioma, leukemia, polycythemia vera, neuroblastoma, retinoblastoma, myeloma, bladder tumor, sarcoma, osteosarcoma, myosarcoma, skin cancer, basal cell cancer, skin appendage cancer, and skin metastatic cancer. The anticancer agent of the present invention may further be applied to benign tumors as well as malignant tumors.

In addition, the anticancer agent of the present invention can be used to suppress cancer metastasis, and particularly is useful as a suppressor of postoperative cancer metastasis.

In the use of the anticancer agent of the present invention, the anticancer agent of the present invention can be administered in various forms to a human or an animal. Examples of the animal other than human preferably include a mammal.

The form of administration of the anticancer agent of the present invention may be oral administration or parenteral administration.

Examples of the parenteral administration include intravenous, intramuscular, subcutaneous or intradermal, intratumoral, intraperitoneal, intraarterial, intramedullary, intracardiac, intraarticular, intrasynovial, intracranial, intrathecal, or subarachnoid (meningeal fluid) injections, rectal administration, and transmucosal administration.

Examples of the form of formulation suitable for oral administration include a tablet, a pill, a granule, a powder, a capsule, a liquid, a suspension, an emulsion, and a syrup.

Examples of the pharmaceutical composition suitable for parenteral administration include an injection, an infusion, a nasal drop, a spray, an inhalant, a suppository, and transdermal absorbents such as an ointment, a cream, a powdery liniment, a liquid liniment, and a patch.

Further examples of the form of formulation of the anticancer agent of the present invention include an implantable pellet and sustained-release formulations based on known techniques.

Among the above, preferred administration form, formulation form, and the like, are appropriately selected by a physician, depending on the age, sex, constitution, and symptoms of the patient, the timing of treatment, and the like.

When the anticancer agent of the present invention is a solid formulation such as a tablet, a pill, a powder, a dust, a granule, or the like, these solid formulations is produced by appropriately mixing the phosphine transition metal complex represented by formula (1) with an appropriate additive in accordance with conventional methods. Examples of the additive include excipients such as lactose, sucrose, D-mannitol, corn starch, synthetic or natural gum, and crystalline cellulose; binders such as starch, hydroxypropylcellulose, hydroxypropylmethylcellulose, rubber arabic, gelatin, and polyvinylpyrrolidone; disintegrating agents such as calcium carboxymethylcellulose, sodium carboxymethylcellulose, starch, corn starch, and sodium alginate; lubricating agents such as talc, magnesium stearate, and sodium stearate; and fillers or diluents such as calcium carbonate, sodium carbonate, calcium phosphate, and sodium phosphate.

The tablet and the like may be subjected to sugar coating, gelatin coating, enteric coating, film coating or the like with a coating agent such as hydroxypropylmethylcellulose, white sugar, polyethylene glycol, titanium oxide or the like, as needed.

One or two or more of each of the additives and the coatings can be used.

When the anticancer agent of the present invention is a liquid formulation such as an injection, an eye drop, a nasal drop, an inhalant, a spray, a lotion, a syrup, a liquid, a suspension, an emulsion, or the like, the liquid formulation is obtained by mixing the phosphine transition metal complex represented by formula (1) with a pharmaceutically acceptable liquid, and dispersing or dissolving the phosphine transition metal complex in the liquid. Examples of the liquid include water such as purified water; appropriate buffers such as phosphate buffer; physiological salt solutions such as saline, Ringer's solution, and lock solution; vegetable oils such as cocoa butter, sesame oil, and olive oil; mineral oil; and organic solvents such as higher alcohol, higher fatty acid, ethanol, and polyhydric alcohol. To the liquid formulation, various additives, for example, emulsifiers such as cholesterol; suspending agents such as gum arabic; dispersion aids; infiltrating agents; surfactants, dissolution aids such as sodium phosphate; stabilizers such as sugar, sugar alcohol, and albumin; preservatives such as paraben; isotonic agents such as sodium chloride, glucose, and glycerin; buffers; painless agents; antiadsorption agents; moisturizers; antioxidants; colorants; sweeteners; flavors; aromatic substances; and the like, may be further added, as needed. Examples of the surfactants include non-ionic surfactants, cationic surfactants, and anionic surfactants. For example, a plurality of surfactants based on polyoxyethylene hardened castor oil and polyoxyethylene sorbitan fatty acid ester, which are polyethylene glycol type non-ionic surfactants, are generally used as pharmaceutical additives.

The liquids and the additives can each be used singly or in combinations of two or more.

The liquid formulation is prepared, for example, as a sterile aqueous solution, a non-aqueous solution, a suspension, a liposome, or an emulsion. Upon this, the injection preferably has a physiological pH, particularly preferably a pH in the range of 6 to 8, at room temperature (25° C.).

When the anticancer agent of the present invention is a semi-solid formulation, such as a lotion, a cream, an ointment and the like, these semi-solid formulations are produced by appropriately mixing the phosphine transition metal complex represented by formula (1) with fat, fatty oil, lanolin, petrolatum, paraffin, wax, a plaster, resin, plastic, glycols, higher alcohol, glycerin, water, an emulsifier, a suspending agent, or the like. The additives can be used singly or in combinations of two or more.

The content of the phosphine transition metal complex represented by formula (1) in the anticancer agent of the present invention varies depending on the administration form, the severity, the amount to be dosed, and the like, but is generally 0.001 to 80% by mass, preferably 0.1 to 50% by mass, based on the total mass of the anticancer agent of the present invention.

The dose of the anticancer agent of the present invention is appropriately determined by a physician depending on the conditions such as the age, sex, body weight and symptoms of the patient and the route of administration, but generally is in the range of about 1 μg/kg to 1,000 mg/kg, preferably in the range of about 10 μg/kg to 10 mg/kg, as the amount of active ingredient per day for an adult. The dose of the anticancer agent may be administered once, or several times (e.g., about two to four times) in portions, a day.

In the use of the anticancer agent of the present invention, the anticancer agent of the present invention can be used in combination with known chemotherapy, surgical therapy, radiation therapy, hyperthermia therapy, immunotherapy, or the like.

All of the above descriptions for the anticancer agent apply to the anticancer agent in the use of the phosphine metal complex represented by formula (1) of the present invention.

The phosphine transition metal complex represented by formula (1) has higher water solubility than the phosphine transition metal complex proposed in Patent Literature 3, so when the phosphine transition metal complex represented by formula (1) is used as an anticancer agent, there are advantages that the administration form and the formulation form can be selected from the wide range, and that the dose can be reduced because it acts effectively on the affected area in small amounts.

EXAMPLES

Hereinafter, the present invention is described in more detail with Examples, but the present invention is not limited to these Examples.

Production Example 1

Synthesis of (R,R)-1,2-bis(t-butylmethylphosphino)benzene

Synthesis of (R)-2-(boranato(t-butyl)methylphosphino)bromobenzene

In accordance with the following reaction formula, (R)-2-(boranato(t-butyl)methylphosphino)bromobenzene was synthesized by the following procedures.

[Formula 12]

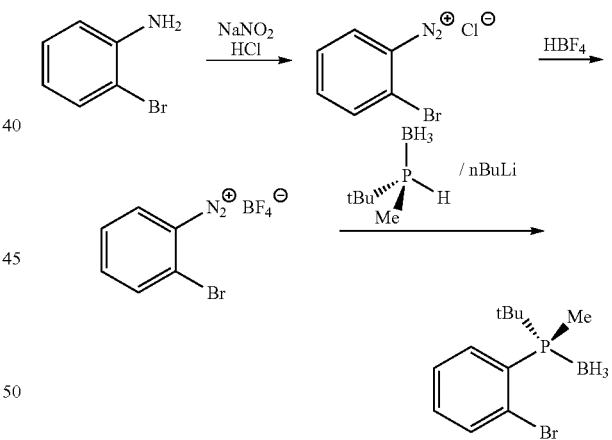

In a 200 mL four-neck flask, 9.5 mL of concentrated hydrochloric acid, 65 mL of pure water, 6.0 g (35 mmol) of 2-bromoaniline were charged, heated, and dissolved. After cooling to 0° C., a solution of 2.46 g (35.1 mmol) of sodium nitrite dissolved in 7.5 mL of pure water in advance was added dropwise over about 10 minutes. The reaction solution was initially gruel-like, but after stirring for 30 minutes, it became a pale yellow clear solution. Then 12.5 g (59.8 mmol) of 42% by mass aqueous $HBF_4$ solution was added dropwise over about 5 minutes to lead immediate precipitation of pale yellow crystals. After stirred for 30 minutes, the crystals were filtered through a glass filter, washed with 30 mL of pure water, and further washed with a mixture solution of 8 mL of methanol and 32 mL of ether. Thereafter, the mixture solution was dried under reduced pressure to obtain 4.5 g (yield 48%) of 2-bromobenzenediazonium tetrafluoroborate.

In a well-dried 30 mL Schrenk tube, 236 mg (2.00 mmol) of (S)-t-butylmethylphosphine-borane was charged. After replacement with Ar, 6 mL of dehydrated tetrahydrofuran (THF) were added, and the mixture was stirred to dissolve. After the solution was cooled to −78° C., 1.5 mL (2.4 mmol) of a solution of nBuLi in hexane (1.6 mol/L) was slowly added. After the mixture was stirred for 20 minutes, 650 mg (2.40 mmol) of the above-described 2-bromobenzenediazonium tetrafluoroborate was added portionwise. The dark red purple clear solution was heated to room temperature over 2 hours, and stirred at room temperature for 2 hours. Saline and ethyl acetate were added, then the organic layer was partitioned, and washed with saline. After drying with MgSO$_4$, the solvent was concentrated and purified by silica gel chromatography to obtain 60 mg (yield 11%) of (R)-2-(boranato(t-butyl)methylphosphino)bromobenzene. The analysis results of the obtained compound are shown below.

(Analysis Results)
$^1$H NMR (500 MHz, CDCl$_3$) δ: 0.20-1.05 (m, 3H), 1.19 (d, J=14.3 Hz, 9H), 1.91 (d, 9.7 Hz, 3H), 7.32 (t, 8.7 Hz, 1H), 7.40 (t, 7.5 Hz, 1H), 7.64 (d, 9.0 Hz, 1H), 8.06 (dd, 12.6, 12.9 Hz, 1H);
$^{31}$P NMR (202 MHz, CDCl$_3$) δ: 38.3.
APCI-MS: m/z 275, 273 (M$^+$+H).

Synthesis of
(R,R)-1,2-bis(t-butylmethylphosphino)benzene
(BenzP*)

In accordance with the following reaction formula, (R,R)-1,2-bis(t-butylmethylphosphino)benzene was synthesized by the following procedures.

[Formula 13]

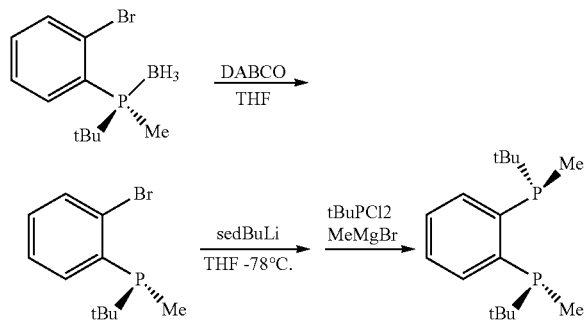

In a well-dried 50 mL two-neck flask, 1.365 g (5.00 mmol) of (R)-2-(boranato(t-butyl)methylphosphino)bromobenzene obtained in the above-described procedures, and 589 mg (5.25 mmol) of 1,4-diazabicyclo[2.2.2]octane (DABCO) were charged. After replacement with Ar, 10 mL of dehydrated tetrahydrofuran was added, and the mixture was stirred to dissolve. The solution was allowed to react for 2 hours at about 70° C. under gentle reflux. The reaction solution was then cooled to −78° C., and then 5.10 mL of a solution of s-butyllithium in hexane (1.03 mol/L) was slowly added by syringe. After 30 minutes, 3 ml of solution of 875 mg (5.5 mmol) of t-butyldichlorophosphine in THF was added in one portion. The mixture was then heated to room temperature over 1 hour, and further stirred for 1 hour. The mixture was then cooled to 0° C. After 12.5 ml of a solution of methylmagnesium bromide in THF (0.96 mol/L) was added by syringe, the mixture was heated to room temperature, and further stirred for 1 hour. The majority of the solvent was then concentrated, and 25 ml of degassed hexane and 10 ml of 15% by mass aqueous NH$_4$Cl solution were added. The hexane layer was separated, then washed with saturated saline, and dried over Na$_2$SO$_4$. The solvent was then concentrated. To the oily residue, degassed methanol was added. The resulting crystal was filtered and washed with a small amount of cooled methanol, then dried under reduced pressure to obtain 539 mg (yield 38%) of (R,R)-1,2-bis(t-butylmethylphosphino)benzene as a colorless crystal. The analysis results of the obtained compound are shown below.

(Analysis Results)
$^1$H NMR (500 MHz, CDCl$_3$) δ: 0.96 (t, J=6.0 Hz, 18H), 1.23 (t, J=3.2 Hz, 6H), 7.26-7.35 (m, 2H), 7.48-7.50 (m, 2H)
$^{13}$C NMR (125 MHz, CDCl$_3$) δ: 5.69 (t, J=6.0 Hz), 27.24 (t, 8.4 Hz), 30.37 (t, 7.2 Hz), 127.75 (S), 131.47 (S), 144.86 (t, 6.0 Hz)
$^{31}$P NMR (202 MHz, CDCl$_3$) δ: −25.20 (s).
APCI-MS: m/z 283 (M$^+$+H).
HRMS (TOF): Calcd. for C$_{16}$H$_{28}$NaP$_2$: 305.1564, Found: 305.1472.
Mp. 125-126° C.
[α]$_D^{24}$: +222.9 (c, 0.535, EtOAc)

Example 1

Synthesis of bis[(R,R)-1,2-bis(t-butylmethylphosphino)benzene]gold(I) chloride (1'-1)

(R,R)-1,2-Bis(t-butylmethylphosphino)benzene (311 mg, 1.1 mmol) and tetrabutylammonium gold(I) dichloride (255 mg, 0.5 mmol) were added to a 25 mL two-neck flask with a stirrer, and pressure reduction and nitrogen introduction were repeated several times to perform nitrogen replacement in system. Dichloromethane (5 mL) was added, and the mixture was stirred for 2 hours, then the solvent was removed by evaporator, and the residue was washed with a small amount of water. The residue was further washed with ethyl acetate and dried under reduced pressure to obtain bis[(R,R)-1,2-bis(t-butylmethylphosphino)benzene]gold(I) chloride represented by the following formula (1'-1) as pale yellow powder (383 mg, crude yield 96%).

The product was dissolved in water (7.5 mL) at about 80° C., and the mixture was slowly cooled to room temperature to lead precipitation of fine needle-like crystal. After further cooled in a refrigerator overnight, the precipitated crystal was collected by filtration, washed with cold water and dried under vacuum in a desiccator to obtain 234 mg of compound of formula (1'-1) (yield 59%).

[Formula 14]

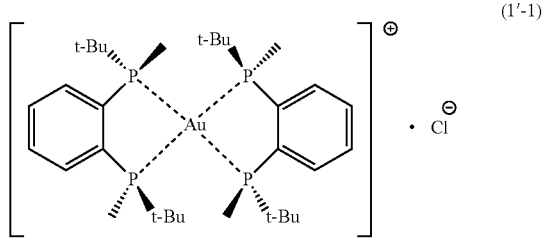

(Analysis Results of Compounds of Formula (1'-1))

$^1$H NMR (500 MHz, CDCl$_3$) δ: 1.128 (m, 36H), 1.842 (s, 12H), 7.62-7.63 (m, 4H), 7.94-7.95 (m, 2H)

$^{13}$C NMR (125 MHz, CDCl$_3$) δ: 13.6, 27.4, 32.5, 127.75 (S), 130.6, 131.7, 141.7-141.9 (m)

$^{31}$P NMR (202 MHz, CDCl$_3$) δ: 20.6 (s).

DART-MS: m/z 761 (C$_{32}$H$_{56}$Au$^+$P$_4$), 515 (C$_{16}$H$_{28}$AuClP$_2$H$^+$), 479 (C$_{16}$H$_{28}$Au$^+$P$_2$)

Example 2

Synthesis of bis[(S,S)-1,2-bis(t-butylmethylphosphino)benzene]gold(I) chloride (1'-2)

The same procedures as in Production Example 1 were performed except that (R)-t-butylmethylphosphino-borane was used in place of (S)-t-butylmethylphosphino-borane in the synthesis of (R)-2-(boranato(t-butyl)methylphosphino)bromobenzene to obtain (S,S)-1,2-bis(t-butylmethylphosphino)benzene.

Then, (S,S)-1,2-bis(t-butylmethylphosphino)benzene (191 mg, 0.675 mmol) and tetrabutylammonium gold(I) dichloride (164 mg, 0.32 mmol) were added to a 25 mL two-neck flask with a stirrer, and pressure reduction and nitrogen introduction were repeated several times to perform nitrogen replacement in system. The same procedures as in Example 1 were performed to obtain 143 mg of the compound of formula (1'-2) as pale yellow crystal (143 mg, 56%).

[Formula 15]

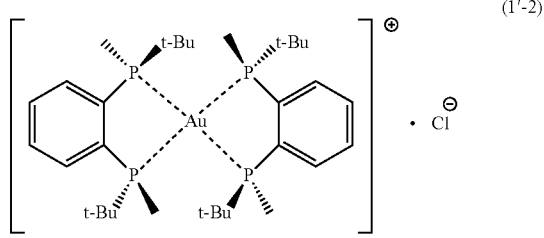

(1'-2)

(Analysis Results of Compounds of Formula (1'-2))

The equivalent results to those of the configuration of Example 1 were obtained in $^1$H NMR, $^{13}$C NMR, $^{31}$P NMR, and DART-MS analyses.

Comparative Example 1

(1) <Synthesis of (R,R)-2,3-bis(tert-butylmethylphosphino)quinoxaline>

(R,R)-2,3-Bis(tert-butylmethylphosphino)quinoxaline was obtained according to the description of Example 1 in Japanese Patent Laid-Open No. 2007-56007 of the previous application of the present applicant.

(2) <Synthesis of bis(2,3-bis(tert-butylmethylphosphino)quinoxaline)gold(I) chloride>

In a 500 ml two-neck flask replaced with nitrogen gas, 5.50 g (16.4 mmol) of (R,R)-2,3-bis(tert-butylmethylphosphino)quinoxaline obtained in the above-described method was dissolved in 220 ml of THF. To this, 4.19 g (8.2 mmol) of tetrabutylammonium gold dichloride was added, and the mixture was stirred at room temperature for 5 hours. The resulting brown precipitate was filtered, then dissolved in 42 ml of dichloromethane, washed with 50 ml of water, and further dried over sodium sulfate. After filtration, the solution was dried and solidified. The solid was dissolved in 50 ml of dichloromethane, then 270 ml of diethyl ether was added, and the mixture was cooled to 0° C., then the solid precipitated to obtain bis(2,3-bis(tert-butylmethylphosphino)quinoxaline)gold(I) chloride. The compound was composed of a compound represented by formula (a-1):

[Formula 16]

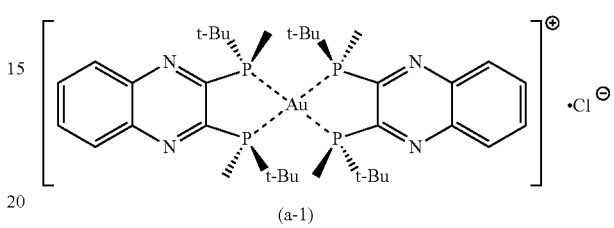

(a-1)

(Analysis Results of Compound of Formula (a-1))

$^{31}$P-NMR (CDCl$_3$); 13.6

[α]$^D$=+195.3 (c=0.5, methanol, 25° C.)

<Solubility Test>

Solubility in aqueous surfactant solutions was evaluated for phosphine transition metal complex samples obtained in Examples 1 and 2 and Comparative Example 1. The solubility was determined by the following HPLC analysis.

[Analyzer]

For the HPLC analyzer, Prominence HPLC system (LC-20AD, Shimadzu Corporation) was used. For the detector, UV detector SPD-20A (Shimadzu Corporation, detection wavelength 249 nm) was used, and for the column, XR-ODS (3 mm i.d.×100 mm, particle diameter 2.2 μm) manufactured by Shimadzu Corporation was used. The mobile phase was methanol:water:TFA=90:10:0.05 (v/v), the column temperature was 40° C., and the flow rate was 0.5 mL/min.

[Sample Preparation]

The samples obtained by Examples 1 and 2 were accurately weighted at 40.01 mg, 50.04 mg and 100.02 mg, and the samples obtained by Comparative Example 1 was accurately weighted at 10.01 mg, 20.02 mg and 30.08 mg, respectively. Each of the weighed samples was placed in 150 μL of surfactants, and the mixture was stirred sufficiently. Then, 850 μL of 5% by mass aqueous glucose solution was added, and the mixture was further stirred at room temperature (25° C.). This solution was passed through a 0.2 μm membrane filter, and the filtrate was diluted 50-fold by volume with methanol:water (9:1) to obtain a preparation solution for HPLC analysis. A mixture of Tween 80 and propylene glycol at a mass ratio of 2:1 was used as the surfactant.

[Analysis]

The prepared samples were transferred to vials, and set in an autosampler. The analysis was performed by injecting each sample by 1 μL.

[Results]

Based on the relationship between the weight of the weighed sample and the area of the peak in the obtained chromatogram, the solubility of the phosphine transition metal complex was evaluated. The results are shown in Table 1.

TABLE 1

| | Solubility (25° C.) |
|---|---|
| Example 1 | 71.4 mq/mL |
| Example 2 | 71.4 mq/mL |
| Comparative Example 1 | 25.5 mg/mL |

<Evaluation of Anticancer Activity>

The evaluation of activity of bis[(R,R)-1,2-bis(t-butylmethylphosphino)benzene]gold(I) chloride (Example 1) and bis[(S,S)-1,2-bis(t-butylmethylphosphino)benzene]gold(I) chloride (Example 2) obtained as described above on tumor cells was performed as follows. As a control, cisplatin was tested in the same way.

A549 (human lung cancer cells), NCI-H460 (human lung cancer cells), MKN45 (human gastric cancer cells), NCI-N87 (human gastric cancer cells), A2780 (human ovarian cancer cells), A2780cis (human ovarian cancer cells, cisplatin-resistant cells) were used as cancer cells, and cultured in Roswell Park Memorial Institute medium (RPMI1640) supplemented with 10 volume % fetal bovine serum and 100 Units/mL penicillin and 100 μg/mL streptomycin under 5 volume % carbon dioxide atmosphere by wet incubation at 37° C.

Cells were washed with phosphate buffered saline (PBS), the cell count was calculated, and then $5 \times 10^4$ cells/ml suspension was prepared using the same medium. The suspension was added to a sterile 96-well microplate at a density of 2500 cells/well.

Bis[(R,R)-1,2-bis(t-butylmethylphosphino)benzene]gold (I) chloride (Example 1) or bis[(S,S)-1,2-bis(t-butylmethylphosphino)benzene]gold(I) chloride (Example 2) fully dissolved in dimethylsulfoxide, or a cisplatin solution was then added, and the mixture was continued to culture in an incubator for 48 hours.

Thereafter, viable cell counts were evaluated by WST-8 assay. In other words, a solution of water-soluble tetrazolium salt WST-8 was added, and then the cells were cultured in an incubator for 1 hour. Absorbance at 450 nm of water-soluble formazan generated by enzymatic activity of mitochondria in cells was measured with a microplate reader (Spectra Max PLUS; Molecular Devices). This was evaluated as viable cell counts, and 50% cell growth inhibitory concentration ($IC_{50}$) was calculated. It should be noted that the mean of the values of three experiments performed in the same way was adopted for the calculation of $IC_{50}$ value. The results are shown in Table 2.

TABLE 2

| | $IC_{50}$ (μM) | | |
|---|---|---|---|
| | Example 1 | Example 2 | Cisplatin |
| A549 | 0.066 | 0.58 | 6.0 |
| NCI-H460 | 0.25 | 0.69 | 3.3 |
| MKN45 | 0.25 | 0.53 | 5.2 |
| NCI-N87 | 1.4 | 2.1 | 42 |
| A2780 | 0.28 | 1.1 | 2.8 |
| A2780cis | 0.095 | 0.56 | 28 |

As is apparent from the results in Table 2, bis[(R,R)-1,2-bis(t-butylmethylphosphino)benzene]gold(I) chloride and bis[(S,S)-1,2-bis(t-butylmethylphosphino)benzene]gold(I) chloride were found to have higher anticancer activity than cisplatin.

INDUSTRIAL APPLICABILITY

The phosphine transition metal complex of the present invention has excellent solubility in an aqueous solvent and can provide an anticancer agent having higher anticancer activity than the conventionally known anticancer agent cisplatin. The method for producing a phosphine transition metal complex of the present invention can industrially advantageously produce the phosphine transition metal complex of the present invention.

The invention claimed is:

1. A phosphine transition metal complex represented by formula (1):

[Formula 1]

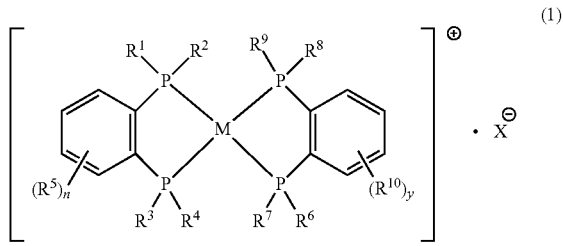

wherein, $R^1$, $R^2$, $R^3$, $R^4$, $R^6$, $R^7$, $R^8$ and $R^9$ each independently represent an optionally substituted linear or branched alkyl group having 1 to 10 carbon atoms, an optionally substituted cycloalkyl group, or an optionally substituted adamantyl group; $R^5$ and $R^{10}$ each independently represent a monovalent substituent; n and y each independently represent an integer of 0 to 4; M represents a transition metal atom selected from the group consisting of gold, copper and silver; $X^-$ represents an anion; and $R^1$ and $R^2$ are different groups from each other, $R^3$ and $R^4$ are different groups from each other, $R^6$ and $R^7$ are different groups from each other, and $R^8$ and $R^9$ are different groups from each other.

2. The phosphine transition metal complex according to claim 1, wherein $R^1$ and $R^6$ are identical groups, $R^2$ and $R^7$ are identical groups, $R^3$ and $R^8$ are identical groups, $R^4$ and $R^9$ are identical groups, $R^5$ and $R^{10}$ are identical groups, and n and y are identical numbers.

3. The phosphine transition metal complex according to claim 1, wherein $R^1$ and $R^2$, and $R^3$ and $R^4$ are combinations of identical two groups; and $R^6$ and $R^7$, and $R^8$ and $R^9$ are combinations of identical two groups.

4. The phosphine transition metal complex according to claim 1, wherein one of $R^1$ and $R^2$ is a methyl group and the other is an optionally substituted branched alkyl group having 3 or more and 10 or less carbon atoms, an optionally substituted cycloalkyl group, or an optionally substituted adamantyl group;

one of $R^3$ and $R^4$ is a methyl group and the other is an optionally substituted branched alkyl group having 3 or more and 10 or less carbon atoms, an optionally substituted cycloalkyl group, or an optionally substituted adamantyl group;

one of $R^6$ and $R^7$ is a methyl group and the other is an optionally substituted branched alkyl group having 3 or more and 10 or less carbon atoms, an optionally substituted cycloalkyl group, or an optionally substituted adamantyl group; and one of $R^8$ and $R^9$ is a methyl group and the other is an optionally substituted branched alkyl group having 3 or more and 10 or less carbon atoms, an optionally substituted cycloalkyl group, or an optionally substituted adamantyl group.

5. The phosphine transition metal complex according to claim 1, wherein $R^1$ and $R^2$, $R^3$ and $R^4$, $R^6$ and $R^7$, and $R^8$ and $R^9$ in formula (1) are all combinations of a t-butyl group and a methyl group.

6. The phosphine transition metal complex according to claim 1, wherein the phosphine transition metal complex has an asymmetric center on four phosphorus atoms in formula (1); and an absolute configuration on the phosphorus atom to which $R^1$ and $R^2$ are bound, an absolute configuration on the phosphorus atom to which $R^3$ and $R^4$ are bound, an absolute configuration on the phosphorus atom to which $R^6$ and $R^7$ are bound, and an absolute configuration on the phosphorus atoms to which $R^8$ and $R^9$ are bound are all identical absolute configurations.

7. The phosphine transition metal complex according to claim 1, wherein M in formula (1) is a gold atom.

8. A method for producing a phosphine transition metal complex, comprising reacting a phosphine derivative represented by formula (2):

[Formula 2]

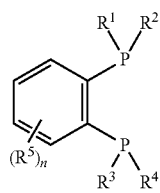

(2)

wherein $R^1$, $R^2$, $R^3$ and $R^4$ each independently represent an optionally substituted linear or branched alkyl group having 1 to 10 carbon atoms, an optionally substituted cycloalkyl group, or an optionally substituted adamantyl group; $R^5$ represents a monovalent substituent; n represents an integer of 0 to 4; and $R^1$ and $R^2$ are different groups from each other, and $R^3$ and $R^4$ are different groups from each other, a phosphine derivative represented by formula (3):

[Formula 3]

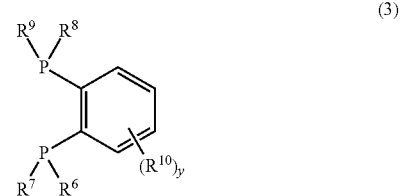

(3)

wherein $R^6$, $R^7$, $R^8$ and $R^9$ each independently represent an optionally substituted linear or branched alkyl group having 1 to 10 carbon atoms, an optionally substituted cycloalkyl group, or an optionally substituted adamantyl group; $R^{10}$ represents a monovalent substituent; y represents an integer of 0 to 4; and $R^6$ and $R^7$ are different groups from each other, and $R^8$ and $R^9$ are different groups from each other, and a salt of a transition metal of gold, copper or silver to obtain a phosphine transition metal complex represented by formula (1):

[Formula 4]

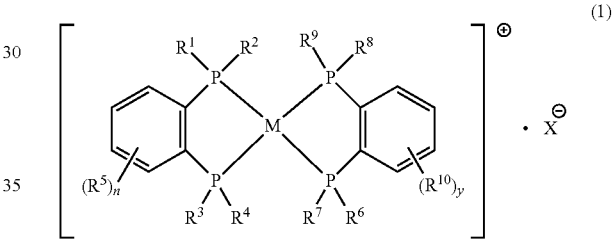

(1)

wherein $R^1$, $R^2$, $R^3$, $R^4$, $R^6$, $R^7$, $R^8$ and $R^9$ each independently represent an optionally substituted linear or branched alkyl group having 1 to 10 carbon atoms, an optionally substituted cycloalkyl group, or an optionally substituted adamantyl group; $R^5$ and $R^{10}$ each independently represent a monovalent substituent; n and y each independently represent an integer of 0 to 4; M represents a transition metal atom selected from the group consisting of gold, copper and silver; $X^-$ represents an anion; and $R^1$ and $R^2$ are different groups from each other, $R^3$ and $R^4$ are different groups from each other, $R^6$ and $R^7$ are different groups from each other, and $R^8$ and $R^9$ are different groups from each other.

9. A medicament comprising the phosphine transition metal complex according to claim 1 as an active ingredient.

10. An anticancer agent comprising the phosphine transition metal complex according to claim 1.

* * * * *